United States Patent [19]

Kitamura et al.

[11] 4,367,323

[45] Jan. 4, 1983

[54] PRODUCTION OF HYDROGELS

[75] Inventors: Shuji Kitamura, Ibaraki; Fumio Fujita; Toshihiro Oonishi, both of Takatsuki; Yoshiharu Tatsukami, Niihama; Masato Ogura, Niihama; Masahiro Niwano, Niihama; Masaru Oota, Niihama; Toshifumi Tamura, Takatsuki, all of Japan

[73] Assignee: Sumitomo Chemical Company, Limited, Osaka, Japan

[21] Appl. No.: 326,651

[22] Filed: Dec. 2, 1981

[30] Foreign Application Priority Data

Dec. 3, 1980 [JP] Japan ................................ 55/170457
Dec. 10, 1980 [JP] Japan ................................ 55/175142

[51] Int. Cl.³ .................................................. C08K 5/09
[52] U.S. Cl. .................................... 526/201; 526/317; 524/460
[58] Field of Search ......................... 526/201; 524/460

[56] References Cited

U.S. PATENT DOCUMENTS

| | | | |
|---|---|---|---|
| 2,987,493 | 6/1961 | Grady et al. | 260/29.6 |
| 3,801,523 | 4/1974 | Shiratsuchi et al. | 260/29.6 RW |
| 3,948,866 | 4/1976 | Pennewis. | |
| 3,975,341 | 8/1976 | Trapasso | 526/303 |
| 4,048,147 | 9/1977 | Arakawa et al. | 260/67 UA |
| 4,093,776 | 6/1978 | Aoki. | |
| 4,226,752 | 10/1980 | Erickson et al. | 260/29.6 RB |
| 4,229,336 | 10/1980 | Sicklesteel et al. | 260/29.6 NR |

FOREIGN PATENT DOCUMENTS 56-2690981 3/1981 Japan.
2032444 5/1980 United Kingdom.

*Primary Examiner*—Joseph L. Schofer
*Assistant Examiner*—Bernard Lipman
*Attorney, Agent, or Firm*—Cushman, Darby & Cushman

[57] ABSTRACT

The invention is to provide the methods for producing highly water-absorbable and water-retainable hydrogels having a large particle diameter together with a sufficient gel strength. The method is characterized by use of a specific dispersing agent in the water-in-oil type inverse phase suspension polymerization of an $\alpha,\beta$-unsaturated carboxylic acid and/or its alkali metal salt. Due to the high water-absorbability and water-retainability, along with the superior gel strength and the stable gel structure, the hydrogels of the invention enlarge the conventional range of usages.

4 Claims, No Drawings

PRODUCTION OF HYDROGELS

The present invention relates to the method for producing hydrogels which are high molecular materials having superior water-absorbability, that is, having the ability to absorb and retain a large amount of water.

More particularly, the invention relates to the method for producing hydrogels of large particle diameter having superior water-absorbability according to an economical and simple procedure.

In recent years, hydrophilic high molecular materials are utilized more and more in the fields of medical industry, food industry and agriculture. In particular, hydrogel which is insoluble in water but hydrophilic and water-absorbable, is gradually utilized as the materials for separation and purification process, such as various membranes and liquid-chromatography carriers, carriers for enzyme immobilization, culture media for microorganisms and plants, medical materials such as contact lense and coating of suture and various other uses utilizing their water-absorbability and water-retainability.

Among these uses, hydrogel employed in such uses where its water-absorbability and water-retainability is to be utilized is desirably that having ability to absorb as large amount of water as possible within a short period of time when contacted with water.

A method has been proposed for the production of a hydrogel suitable for those uses, which method is to produce a highly water-absorbable hydrogel consisting of a self-crosslinking alkali acrylate polymer, by polymerizing an aqueous alkali acrylate solution in the presence of a fatty acid sorbitan ester having H.L.B. of 3 to 6. (For example, Japanese Unexamined Published Patent Application No. 46389/1978).

The hydrogel produced according to this method has the average polymer particle diameter of 40 to 50 $\mu$m, as shown in the examples of the Patent Application.

If the average particle diameter of hydrogel is so small, gaps between the particles are filled with water upon absorption of water, so that the hydrogel feels wet. For instance, when the hydrogel is mixed with a soil to be utilized as a soil water-retaining agent, the balance of the three-phase structure of solid-liquid-gas is lost, causing the excessively wet soil, so that the soil is not suitable for growing plants. When the hydrogel having a smaller particle diameter is used for disposable diaper, tampon, sanitary cotton, napkin, and the like other usages where they contact directly to human body, it has such drawbacks as yielding the unfavorable wet feeling.

Accordingly, the production of hydrogel having a larger particle diameter has been keenly desired.

In view of such circumstances, the present inventors have exhaustively investigated the method for producing a highly water-absorbable hydrogel which has a large average particle diameter together with a sufficient gel strength. They have thus accomplished the present invention based upon their findings that a hydrogel having a large average particle diameter can be produced by using a specific compound as the dispersing agent.

Accordingly, the object of the present invention is to provide the method for producing highly water-absorbable hydrogels having a large particle diameter together with a sufficient gel strength, which method comprises that, in producing the hydrogel by water-in-oil type inverse phase suspension polymerization of an $\alpha,\beta$-unsaturated carboxylic acid monomer and/or its alkali metal salt with or without a cross-linking agent, a carboxyl-containing polymer having affinity to the organic solvent is used as the dispersing agent.

The subject of the method of the present invention is demonstrated within the method of polymerizing an $\alpha,\beta$-unsaturated carboxylic acid monomer and/or its alkali metal salt in the presence or absence of a cross-linking agent according to the water-in-oil type inverse phase suspension polymerization process.

According to the method of the present invention, hydrogels having 100 to 3000 $\mu$m of the particle diameter can be produced. The obtainment of such large particle diameter of the hydrogel is due to the use of the dispersion stabilizing agent in the water-in-oil type inverse phase suspension polymerization process.

It has been known that the particle diameter of the suspended particles in a dispersion of two phases such as water-oil is primarily subject to the influence of the following three factors. The first is the agitating power in stirring, the second the surface tension between the two phases, and the third the viscosity of the system. The higher dispersibility yields particles of finer or smaller particle diameter, but the too low dispersibility does not yield suspension and dispersion of the particles.

The carboxyl-containing polymers employed as the dispersing agent in the present invention should essentially be those having affinity to organic solvent.

The "affinity" as referred to in the description of the invention means to be completely or partially soluble in the organic solvent used as the polymerization medium.

As the carboxyl-containing polymers, those having not less than 0.01 mol %, preferably 0.1 to 50 mol %, of carboxyl group may be used in general.

Those having less than 0.01 mol % of carboxyl group are not favorable, since they do not allow the water-in-oil type inverse phase suspension polymerization and thus fail to yield a large particle diameter of the hydrogel.

Any of the carboxyl-containing polymers may be employed so far as it has the affinity to organic solvent. Ordinarily, copolymers of a carboxyl-containing monomer with another ethylenically unsaturated monomer, polymers obtained by reaction of a carboxyl-containing monomer with a homo- or copolymer of an ethylenically unsaturated monomer, graft copolymers obtained by graft polymerization of a carboxyl-containing monomer on a homo- or copolymer of an ethylenically unsaturated monomer and the modified products thereof may be employed.

As the carboxyl-containing monomer, there may be illustrated $\alpha,\beta$-unsaturated carboxylic acids such as acrylic acid, methacrylic acid and the like and hydroxyalkyl $\alpha,\beta$-unsaturated carboxylates such as hydroxyethyl acrylate, hydroxyethyl methacrylate, hydroxypropyl acrylate, hydroxypropyl methacrylate and the like.

As the ethylenically unsaturated monomer, there may be illustrated olefins such as ethylene, propylene, butenes, butadiene and the like; vinyl esters such as vinyl acetate, vinyl propionate, vinyl butyrate and the like; vinyl ethers such as butyl vinyl ether, 2-ethylhexyl vinyl ether, cetyl vinyl ether, stearyl vinyl ether and the like; acrylate esters such as ethyl acrylate, butyl acrylate, 2-ethylhexyl acrylate and the like; and methacrylate esters such as methyl methacrylate, ethyl methacrylate, butyl methacrylate, 2-ethylhexyl methacrylate and the like.

Preferably there may be illustrated ethylene-acrylic acid copolymer, maleic anhydride-modified product from ethylene-vinyl acetate copolymer, methyl methacrylate-methacrylic acid-2-ethylhexyl acrylate copolymer, the reaction product of maleic anhydride-modified liquid polybutadiene and 2-hydroxyethyl methacrylate, polybutadiene-butyl methacrylate-methacrylic acid copolymer, ethylene-propylene-monomeric diene copolymer (hereinafter referred to as EPDM)-acrylic acid-ethyl methacrylate graft copolymer, EPDM-acrylic acid-butyl methacrylate graft copolymer, EPDM-acrylic acid-2-ethylhexyl methacrylate graft copolymer, EPDM-methacrylic acid-2-hydroxyethyl methacrylate graft copolymer, EPDM-methacrylic acid-ethyl methacrylate graft copolymer, EPDM-methacrylic acid-butyl methacrylate graft copolymer, EPDM-methacrylic acid-2-ethylhexyl methacrylate graft copolymer, EPDM-methacrylic acid-2-hydroxyethyl methacrylate graft copolymer and the like.

More preferably, there may be employed methyl methacrylate-methacrylic acid-2-ethylhexyl acrylate copolymer having component ratio (by weight) of 0–16:2–10:98–74, the reaction product of maleic anhydride-modified liquid polybutadiene with 2-hydroxyethyl methacrylate wherein the modified polybutadiene is obtained by the reaction of polybutadiene having 500 to 5000 of molecular weight with 0.1 to 20% by weight of maleic anhydride, polybutadiene-butyl methacrylate-methacrylic acid graft copolymer, EPDM-methacrylic acid-butyl methacrylate or EPDM-methacrylic acid-ethyl methacrylate graft copolymer containing 10 to 95% by weight of EPDM. The carboxyl-containing polymer employed may be that having a molecular weight higher than oligomer (that is, not less than 500 of molecular weight).

In carrying out the present invention, the carboxyl-containing polymer as the dispersing agent is added to the organic solvent in an amount of 0.01 to 20% by weight, preferably 0.05 to 10% by weight per the amount of the monomer to be fed. An amount of the dispersing agent less than 0.01% by weight adversely affects the dispersion stability in the polymerization and difficulty yields hydrogel of beads form having a large particle diameter. On the other side, an amount more than 20% by weight gives too high viscosity of the polymerization system, so that unfavorably it gives smaller particle diameter of the hydrogel, which causes, also, necessity of troublesome washing process.

As the $\alpha,\beta$-unsaturated carboxylic acid monomers and/or their alkali metal salt monomers employed in the method of the present invention, there may be illustrated acrylic, methacrylic, itaconic, crotonic, maleic, and fumaric acids, and their alkali metal salts.

As the particularly suitable ones among them, acrylic and methacrylic acids, and their alkali metal salts may be illustrated.

As the alkali metals, there may be mentioned sodium, potassium, calcium, barium and others.

It is needless to say that any other ethylenically unsaturated monomer may be copolymerized within the scope of the object to produce the present hydrogel.

To practice the method of the present invention, any of the publicly known organic solvents, such as aliphatic hydrocarbons, for example, hexane, heptane and the like, alicyclic hydrocarbons, for example, cyclohexane and the like, and aromatic hydrocarbons, for example, benzene, toluene, xylene, and the like, may be used as the polymerization medium.

In the polymerization, the $\alpha,\beta$-unsaturated carboxylic acid monomer and/or its alkali metal salt is used in a concentration in the organic solvent generally within the range from 5 to 50% by weight. While, the ratio of water/organic solvent (in weight) is generally within the range of 0–50/100–50.

In the method of the present invention, the polymerization may be carried out in the presence or absence of a cross-linking agent or a bridging agent. Such conditions may be adequately selected according to the objective usage of the hydrogel.

As the cross-linking agent or the bridging agent employed in case of the polymerization where it is necessitated, it may be any of those copolymerizable with the $\alpha,\beta$-unsaturated carboxylic acid monomer and/or its alkali salt monomer, and there may be exemplified di- or tri-(meth)acrylate esters of polyols, such as ethylene glycol, propylene glycol, trimethylolpropane, glycerol, polyoxyethylene glycol, polyoxypropylene glycol and the like, unsaturated polyesters obtained by reacting unsaturated acids such as maleic and fumaric acids with the abovementioned polyols, bis-acrylamides, such as N,N'-methylenebisacrylamide, di- or tri-(meth)acrylate esters, obtained by reacting (meth)acrylic acid with a polyepoxide, di-(meth)acrylate carbamate esters obtained by reacting hydroxyethyl (meth)acrylate with polyisocyanates, such as tolylene diisocyanate, hexamethylene diisocyanate and the like, allylated starch, allylated cellulose, diallyl phthalate, N,N',N''-triallyl isocyanurate, divinylbenzene, and the like.

Particularly preferred are ethylene glycol diacrylate, ethylene glycol dimethacrylate, diethylene glycol diacrylate, diethylene glycol dimethacrylate, propylene glycol diacrylate, propylene glycol dimethacrylate, polyethylene glycol diacrylate, polyethylene glycol dimethacrylate, diallyl phthalate, N,N',N''-triallyl isocyanurate, N,N'-methylenebisacrylamide and the like.

The cross-linking agent is generally used in the proportion of 0.001 to 1% by weight, preferably 0.01 to 0.5% by weight.

In practicing the present method of the invention, the amount of the polymerization catalyst employed is generally within the range from 0.01 to 1% by weight per the amount of the monomer.

As for the polymerization catalyst, an aqueous soluble catalyst is used, since the polymerization is effected in the aqueous phase in the inverse phase suspention polymerization. Such catalyst may be 2,2'-azobis(2-aminodipropane)hydrochloride, potassium persulfate, ammonium persulfate or hydrogen peroxide or its combination system with a suitable reducing agent such as sodium hydrogen sulfite, sodium thiosulfate, sodium pyrosulfite, Rongalite and the like.

The polymerization reaction may generally be carried out at a temperature between 40° and 100° C. under stirring condition.

Any of the publicly known dispersing agent such as sorbitan monostearate may be combinedly used in practicing the present method of the invention.

The polymerization reaction product is then separated from the organic solvent by, for example, sedimentation, filtration, centrifugation, etc., washed, if necessary, and dried to recover hydrogel, although such procedure is not limitative.

The hydrogels produced according to the method of the present invention as minutely described above varies depending upon the kind of the dispersing agent and its amount used. In general, however, hydrogel having a voluntarily controlled average particle diameter within the range from about 50 to 3000 μm can be produced.

Further, the method of the present invention ensures the production of the hydrogel having favorable particle form by use of even a comparatively small amount of the dispersing agent.

Moreover, the hydrogel having a large particle diameter produced according to the method of the present invention displays the advantage in that it enlarges the range of usages of hydrogel, since it possesses a sufficient gel strength and superior water-absorbability.

The highly water-absorbable hydrogel according to the present invention provides for the advantages as follows. It is transparent, less colored and almost nontoxic as easily presumed from the constituted molecular structure. Therefore, it is expected to be used for various sanitary materials, for example, disposable diaper, tampon, sanitary cotton, bandage, napkin and other usages where they contact to human body, without any obstacle. Due to its superior gel strength in its water-absorbing state along with less tendency of its gel structure to be collapsed after a long period of usage, it may be suitably used in various commercial uses, for instance, separating agent for water in oil, other dehydrating or drying agent, water-retaining agent for plant and soil, liquid chromatography carrier and other usages where its water-absorbing and water-retaining abilities are utilized. It is also other advantages that the highly water-absorbable hydrogel of the present invention can be produced commercially with extreme easiness and can be shaped in various forms depending on the usages.

The hydrogel according to the present invention may be added with coloring agent, perfumery or other additives or various inorganic and organic fillers. Furthermore, the present hydrogel may be used compositely with paper, fiber, textile and other different materials.

Hereunder, the method of the present invention will more concretely be described in reference to the working examples which, however, should not be construed to be limitative.

In the examples, the water-absorbing ability of the hydrogel is exhibited by the following formula.

$$\text{Water-absorbing ability (g/g)} = \frac{\text{Weight of hydrogel after water absorbing (g)}}{\text{Weight of dry hydrogel (g)}}$$

The average particle diameter is determined by a screening method.

The gel strength is represented by the strength against collapsing compression of absorbed water-saturated gel particles, as shown by the following formula.

$$\text{gel strength} = \frac{\text{Collapsing load}}{\pi(\text{radius of absorbed water-saturated hydrogel particle})^2}$$

EXAMPLE 1

Preparation of carboxyl-containing polymer

In 100 g of water placed in a 200 ml-volume flask were dissolved 0.1 g of polyvinyl alcohol (degree of polymerization of 1700 and degree of saponification of 88%) and then 4 g of sodium chloride. Into the solution were added 19.8 g of 2-ethylhexyl acrylate, 0.5 g of methacrylic acid, 1.25 g of methyl methacrylate, 0.005 g of dodecyl mercaptan, and 0.1 g of lauroyl peroxide. The mixture was allowed to polymerize at temperature of 60° C. for 6 hours. The resulting suspension particles were separated by filtration, washed with water and dried, to give 2-ethylhexyl acrylate/methacrylic acid/methyl methacrylate copolymer.

Production of hydrogel (1)

In a 300 ml-volume flask, 1.5 g of the carboxyl-containing copolymer prepared as mentioned above was dissolved in 150 ml of hexane. Into a mixture of 20 ml of water, 15 g of acrylic acid and 6.7 g of sodium hydroxide, were added 15 mg of potassium persulfate and 3 mg of N,N'-methylenebisacrylamide. The resulting aqueous sodium acrylate solution was dropped into the hexane solution under 250 r.p.m. stirring at temperature of 60° C. during 3 hours to effect the polymerization. Thereafter, the polymer was separated by filtration and dried in vacuo at temperature of 80° C. for 10 hours. The resulting hydrogel had the average particle diameter of 300 μm and the water-absorbing ability of 550 g/g. The absorbed water-saturated hydrogel had the strength of 550 g/cm².

Production of hydrogel (2)

In a 300 ml-volume flask, 1.5 g of the carboxyl-containing copolymer prepared as mentioned above was dissolved in 150 ml of hexane. Into a mixture of 20 ml of water, 15 g of acrylic acid and 6.7 g of sodium hydroxide was added 30 mg of potassium persulfate. The resulting aqueous sodium acrylate solution was dropped into the hexane solution under 350 r.p.m. stirring at temperature of 60° C. during 3 hours to effect the polymerization. Then, the polymer was separated by filtration and dried in vacuo at temperature of 80° C. for 10 hours. The resulting hydrogel had the average particle diameter of 250 μm and the water absorbing ability of 900 g/g. The absorbed water-saturated hydrogel had the strength of 350 g/cm².

EXAMPLE 2

Preparation of carboxyl-containing polymer

Into a mixture of 13.5 g of liquid polybutadiene (high cis-1,4-type polybutadiene, molecular weight 1700) and 0.027 g of iron naphthenate placed in a 200 ml-volume flask was added 1.5 g of maleic anhydride. The mixture was heated up to temperature of 190° C. under nitrogen gas stream and allowed to react under stirring for 4 hours to give maleic anhydride-modified liquid polybutadiene.

To 10 g of the resulting maleic anhydride-modified liquid polybutadiene were added 1.99 g of 2-hydroxyethyl methacrylate, and then 0.012 g of hydroquinone monomethyl ether, 5.64 g of toluene and 0.154 g of triethylamine. The mixture was allowed to react at temperature of 75° to 80° C. for 3 hours, to give a half-esterified compound of maleic anhydride-modified liquid polybutadiene with 2-hydroxy-ethyl methacrylate.

Production of hydrogel (1)

In a 300 ml-volume flask, 0.5 g of the carboxyl-containing copolymer (the half-esterified compound prepared as mentioned above; 5.2 mol % of carboxyl-content) was dissolved in 150 ml toluene. Into a mixture of 20 ml of water, 15 g of acrylic acid and 6.7 g of sodium hydroxide were added 15 mg of potassium persulfate and 3 mg of N,N'-methylenebisacrylamide. The resulting aqueous sodium acrylate solution was dropped into the toluene solution under 250 r.p.m. stirring at temperature of 70° C. during 3 hours to effect the polymerization. Thereafter, the polymer was separated by filtration and dried in vacuo at temperature of 80° C. for 10 hours. The resulting hydrogel had the average particle diameter of 170 μm and the water-absorbing ability of 460 g/g. The absorbed water-saturated hydrogel had the strength of 800 g/cm$^2$.

Production of hydrogel (2)

In a 300 ml-volume flask, 0.5 g of the carboxyl-containing copolymer (the half-esterified compound prepared as mentioned above) was dissolved in 150 ml of toluene. Into a mixture of 20 ml of water, 15 g of acrylic acid and 6.7 g of sodium hydroxide was added 50 mg of potassium persulfate. The resulting aqueous sodium acrylate solution was dropped into the toluene solution under 250 r.p.m. stirring at temperature of 70° C. during 3 hours. Thereafter, the polymer was separated by filtration and dried in vacuo at temperature of 80° C. for 10 hours. The resulting hydrogel had the average particle diameter of 170 μm and the water-absorbing ability of 1000 g/g. The absorbed water-saturated hydrogel had the strength of 500 g/cm$^2$.

EXAMPLE 3

Preparation of carboxyl-containing polymer

In a 500 ml-volume flask, a mixture of 22 g of EPDM (ESPRENE® 501A, manufactured by Sumitomo Chemical Co., Ltd.) and 270 g of hexane was heated for dissolution. Four grams of methacrylic acid, 4 g of butyl methacrylate and 0.3 g of azobisisobutyronitrile were added thereto. The mixture was covered by nitrogen atmosphere and stirred at temperature of 60° C. for 7 hours for reaction, to give a hexane emulsion of the carboxyl-containing polymer.

Production of hydrogel

In a 500 ml-volume flask, 14 g of the hexane emulsion mentioned above and 200 ml hexane were mixed well together by stirring. While, into a mixture of 27 ml of water, 20 g of acrylic acid and 9 g of sodium hydroxide were added 20 mg of potassium persulfate and 4 mg of N,N'-methylenebisacrylamide. The resulting aqueous sodium acrylate solution was dropped into the hexane emulsion under 450 r.p.m. stirring at temperature of 60° C. during 3 hours. The resulting polymer was separated by filtration and dried in vacuo at temperature of 80° C. for 10 hours. The resulting hydrogel had the average particle diameter of 700 μm, the water-absorbing ability of 520 g/g and the gel strength of 600 g/cm$^2$.

EXAMPLE 4

Preparation of carboxyl-containing polymer

In a 500 ml-volume flask, a mixture of 22 g of EPDM (ESPRENE® 501A, manufactured by Sumitomo Chemical Co., Ltd.) and 270 g of cyclohexane was heated for dissolution. Four grams of methacrylic acid, 6 g of ethyl methacrylate and 0.3 g of azobisisobutyronitrile were added thereto. The mixture was covered by nitrogen gas stream and stirred at temperature of 75° C. for 7 hours for the reaction to give a cyclohexane emulsion of the carboxyl-containing polymer.

Production of hydrogel

In a 500 ml-volume flask, 14 g of the cyclohexane emulsion and 200 ml of cyclohexane were mixed well together by stirring. While, into a mixture of 27 ml of water, 20 g of acrylic acid and 9 g of sodium hydroxide was added 40 mg of potassium persulfate. The resulting aqueous sodium acrylate solution was added to the cyclohexane emulsion under 450 r.p.m. stirring at temperature of 60° C. during 3 hours to effect the polymerization. Thereafter, the resulting polymer was separated by filtration and dried in vacuo at temperature of 80° C. for 10 hours. The resulting hydrogel had the average particle diameter of 400 μm, the water-absorbing ability of 910 g/g and the gel strength of 300 g/cm$^2$.

EXAMPLE 5

Preparation of carboxyl-containing polymer

In a 500 ml-volume flask, 15 g of EPDM (ESPRENE® 510A, manufactured by Sumitomo Chemical Co., Ltd.) and 270 g of heptane were heated for dissolution. Then, 6 g of methacrylic acid, 9 g of 2-hydroxyethyl methacrylate and 0.03 g of dicumyl peroxide were added thereto. The mixture was stirred at temperature of 60° C. for 7 hours for the reaction to give a heptane emulsion of the carboxyl-containing polymer.

Production of hydrogel

In a 500 ml-volume flask, 20 g of the heptane emulsion mentioned above and 200 ml of heptane were mixed well together by stirring. While, into a mixture of 27 ml of water, 20 g of acrylic acid and 9 g of sodium hydroxide were added 20 mg of potassium persulfate and 4 mg of N,N'-methylenebisacrylamide. The resulting aqueous sodium acrylate solution was added to the heptane emulsion under 500 r.p.m. stirring at temperature of 70° C. during 3 hours to effect the polymerization. Thereafter, the resulting polymer was separated by filtration and dried in vacuo at temperature of 80° C. for 10 hours. The resulting hydrogel had the average particle diameter of 200 μm, the water-absorbing ability of 600 g/g and the gel strength of 530 g/cm$^2$.

EXAMPLE 6

Preparation of carboxyl-containing polymer

A mixture of 40 g of liquid polybutadiene (SUMIKAOIL® #150, manufactured by Sumitomo Chemical Co., Ltd.), 5 g of n-butyl methacrylate, 5 g of methacrylic acid, 0.5 g of benzoyl peroxide and 50 g of hexane, placed in a 200 ml-volume flask, was covered by nitrogen gas atmosphere and stirred at temperature of 68° C. for 4 hours to effect the reaction, to give a semi-transparent solution of the carboxyl-containing polymer.

Production of hydrogel

In a 500 ml-volume flask, 250 ml of hexane and 1 g of the hexane solution of the graft polymer mentioned above were stirred for complete dissolution. Further, 28 g of acrylic acid, 49 g of an aqueous 25.3% by weight sodium hydroxide solution and 50 mg of potassium persulfate were added thereto. The mixture was allowed to react at temperature of 62° C. in nitrogen atmosphere under 500 r.p.m. stirring for 4 hours. Thereafter, the resulting polymer was separated by filtration and dried in vacuo at temperature of 80° C. for 10 hours.

The resulting hydrogel had the average particle diameter of 160 μm and the water-absorbing ability of 1100 g/g.

EXAMPLE 7

In a 300 ml-volume flask, 0.5 g of ethylene-acrylic acid copolymer (containing 20% by weight acrylic acid) was dissolved in 150 ml of toluene. On the other side, into a mixture of 20 ml of water, 15 g of acrylic acid and 6.7 g of sodium hydroxide, were added 15 mg of potassium persulfate and 10 mg of polyethylene glycol diacrylate (the molecular weight of the polyethylene glycol, 400). The resulting aqueous sodium acrylate solution was dropped into the toluene solution of the carboxyl-containing polymer mentioned above under 250 r.p.m. stirring at temperature of 70° C. during 3 hours to effect polymerization. Thereafter, the polymer was separated by filtration and dried in vacuo at temperature of 80° C. for 10 hours. The resulting hydrogel had the average particle diameter of 240 μm and the water-absorbing ability of 580 g/g.

COMPARATIVE EXAMPLE 1

In a 300 ml-volume flask, 0.9 g of sorbitan monostearate was dissolved in 100 ml of hexane. On the other side, into a mixture of 20 ml of water, 15 g of acrylic acid and 6.7 g of sodium hydroxide, were added 15 mg of potassium persulfate and 3 mg of methylenebisacrylamide. The resulting aqueous sodium acrylate solution was dropped into the hexane solution of sorbitan monostearate under 250 r.p.m. stirring at temperature of 60° C. during 3 hours to effect polymerization.

Thereafter, the polymer was separated by filtration and dried in vacuo at temperature of 80° C. for 10 hours. The resulting hydrogel had the average particle diameter of as small as 45 μm, the water-absorbing ability of 400 g/g and the gel strength of 150 g/cm$^2$.

COMPARATIVE EXAMPLE 2

In a 300 ml-volume flask, 0.9 g of sorbitan monostearate was dissolved in 100 ml hexane. On the other side, into a mixture of 20 ml of water, 15 g of acrylic acid and 6.7 g of sodium hydroxide was added 50 mg of potassium persulfate. The resulting aqueous sodium acrylate solution was dropped into the hexane solution of sorbitan monostearate under 250 r.p.m. stirring at temperature of 62° C. during 3 hours to effect the polymerization.

Thereafter, the polymer was separated by filtration and dried in vacuo at temperature of 80° C. for 10 hours. The resulting hydrogel had the average particle diameter of as small as 50 μm and the water-absorbing ability of 450 g/g. The gel strength was unmeasurable.

REFERENCE EXAMPLE 1

Ten grams of kraft pulp dipped in 1 liter of water was beated well by a mixer. The mixture was mixed with 1 liter of methanol and 5 g of the hydrogel obtained in Example 1 [hydrogel (2)], paper-made on an 80 mesh wire gauze, and dried in a hot wind, to give a hydrogel-filled paper. The paper showed the water-absorbing rate (using an artificial urine) of 75 g/g. While, the hydrogel-filled paper manufactured in similar way but using 5 g of the hydrogel obtained in Comparative example 2, showed the water-absorbing ability (using an artificial urine) of 17 g/g.

REFERENCE EXAMPLE 2

To 500 g of a sandy soil was well mixed 1 g of the hydrogel obtained in Example 1 [hydrogel (1)] or 1 g of the hydrogel obtained in Comparative example 1. These soils, as well as soil not added with any hydrogel, were planted each with egg-plant seedlings, and sprinkled with each 200 cc of water once per 3 days. After a week cultivation of the seedlings, the egg-plants in the soil not added with any hydrogel had withered, and those in the soil added with the hydrogel of Comparative example 1 had suffered from root rot. While, the egg-plants planted in the soil added with the hydrogel (1) in Example 1 were growing normally.

We claim:

1. A method for producing hydrogels which comprises that, in producing the hydrogel by water-in-oil type inverse phase suspension polymerization of an α,β-unsaturated carboxylic acid monomer and/or its alkali metal salt in the presence or absence of a crosslinking agent, a carboxyl-containing polymer having affinity to the organic solvent is used as the dispersing agent.

2. The method for producing hydrogels according to claim 1, wherein the carboxyl-containing polymer is selected from the group consisting of methacrylic acid-methyl acrylate-2-ethylhexyl acrylate copolymer; reaction product from maleic anhydride-modified liquid polybutadiene and 2-hydroxyethyl methacrylate; graft polymer of ethylene-propylene-monomeric diene copolymer grafted with an α,β-unsaturated carboxylic acid and an alkyl or hydroxyalkyl α,β-unsaturated carboxylate; and polybutadiene-butyl methacrylate-methacrylic acid graft copolymer.

3. The method for producing hydrogels according to claim 1, wherein the α,β-unsaturated carboxylic acid is any of acrylic acid and methacrylic acid.

4. The method for producing hydrogels according to claim 1, wherein the organic solvent is any of hexane, heptane, cyclohexane, benzene, xylene and toluene.

* * * * *